United States Patent [19]
Shen et al.

[11] Patent Number: 5,786,514
[45] Date of Patent: Jul. 28, 1998

[54] PROCESS FOR ALKOXYLATING CARBONYL-FUNCTIONALIZED PHENOLS USING DOUBLE METAL CYANIDE CATALYSTS

[75] Inventors: Jianzhong Shen, West Chester; Sujuan Ba, Wayne; David M. Braunstein, Berwyn; Haven S. Kesling, Jr., Drexel Hill, all of Pa.

[73] Assignee: Arco Chemical Technology, L.P., Greenville, Del.

[21] Appl. No.: 769,197

[22] Filed: Dec. 18, 1996

[51] Int. Cl.⁶ ................................................ C07C 45/70
[52] U.S. Cl. .................................. 568/315; 568/337
[58] Field of Search .................................. 568/315, 337

[56] References Cited

U.S. PATENT DOCUMENTS

| | | | |
|---|---|---|---|
| 3,829,505 | 8/1974 | Herold | 260/611 |
| 4,727,199 | 2/1988 | King | 568/315 |
| 5,158,922 | 10/1992 | Hinney et al. | 502/175 |
| 5,346,983 | 9/1994 | Sheehan et al. | 528/212 |
| 5,470,813 | 11/1995 | Le-Khac | 502/175 |
| 5,482,908 | 1/1996 | Le-Khac | 502/156 |
| 5,545,601 | 8/1996 | Le-Khac | 502/156 |

*Primary Examiner*—James H. Reamer
*Attorney, Agent, or Firm*—Jonathan L. Schuchardt

[57] ABSTRACT

A process for alkoxylating phenols is disclosed. The process comprises reacting a carbonyl-functionalized phenol with an alkylene oxide in the presence of a substantially non-crystalline double metal cyanide (DMC) catalyst. The process offers fast reaction times at low catalyst levels, reduced problems with condensation side reactions, and low-color, low-viscosity, low-polydispersity alkoxylated phenols. The process enables efficient preparation of alkoxylated carbonyl-functonalized phenols that are especially valuable in the surfactant industry.

19 Claims, No Drawings

PROCESS FOR ALKOXYLATING CARBONYL-FUNCTIONALIZED PHENOLS USING DOUBLE METAL CYANIDE CATALYSTS

FIELD OF THE INVENTION

The invention relates to a process for alkoxylating phenols. In particular, the invention is a process for alkoxylating, via double metal cyanide catalysis, phenols that contain a carbonyl functional group. Alkoxylated carbonyl-functionalized phenols are valuable chemical intermediates for making surfactants. In addition, they can be aminated and used in dispersants, surfactants, clear epoxy castings, polyamides, and polyurethanes.

BACKGROUND OF THE INVENTION

Alkoxylated phenols that have carbonyl functionalities are valuable in the surfactant industry. The phenolic hydroxyl is alkoxylated with propylene oxide, ethylene oxide, or both to achieve any desired degree of hydrophilicity or hydrophobicity. The carbonyl functional group is often converted to an amine salt to make a polar head.

Phenols are usually alkoxylated with an alkaline catalyst such as sodium or potassium hydroxide. The phenol is combined with aqueous base, and water is removed by vacuum stripping at elevated temperature to give a phenolate salt. Epoxide is then added to the phenolate salt to add the desired number of oxyalkylene units per molecule. U.S. Pat. No. 5,346,983, for example, shows how to make alkoxylated phenols this way. This reference teaches that up to 1000 oxyalkylene units can be added, and shows examples of an ethoxylated phenol having an average of 81 oxyethylene units per molecule, and a propoxylated phenol having an average of 11 oxypropylene units per molecule.

Unfortunately, base-catalyzed alkoxylation of carbonyl-functionalized phenols suffers from some drawbacks. Condensation reactions (e.g., aldol condensations) compete with alkoxylation, resulting in a large proportion of undesired high-molecular-weight side products. Acid-catalyzed alkoxylation of carbonyl-functionalized phenols is also plagued by competing condensation reactions. In addition, acid-catalyzed alkoxylation also tends to produce cyclic ether by-products. Side reactions in both acid and base-catalyzed processes contribute to an undesirably high level of color, high viscosity, and high polydispersity in the alkoxylated phenol. The issue of side reactions becomes even more prominent when the desired reaction product has more than about five oxyalkylene units, especially when propylene oxide is used. Consequently, it is extremely difficult to make a high-quality propoxylated carbonyl-functionalized phenol having an average of more than about five oxypropylene units.

Double metal cyanide (DMC) compounds are well-known catalysts for making epoxide polymers, including alkoxylated phenols. U.S. Pat. No. 3,829,505 teaches to use phenols as telogens (starters) for making propoxylated phenols using these catalysts. For example, the reference shows (Table E) the preparation of 1500–2000 molecular weight propoxylated phenols from the reaction of resorcinol or bisphenol A with propylene oxide in the presence of a zinc hexacyanocobaltate-glyme complex. Interestingly, the same reference teaches that ketones (e.g., acetone) can also be used as telogens, so a skilled person might expect propoxylation of both phenolic hydroxyl and enol hydroxyl (from tautomerization of the ketone) groups when the telogen contains both a phenolic hydroxl group and enolizable hydrogens (as in, e.g., 4-hydroxy-acetophenone).

The conventional DMC catalysts described above offer the advantage of reduced side reactions because these catalysts generally do not promote condensation reactions or cyclic ether formation. Thus, it is possible to make low-color, relatively pure alkoxylated carbonyl-functionalized phenols with DMC catalysts. Unfortunately, however, the catalysts described in the early DMC catalyst literature are generally not active enough to make preparation of the alkoxylated phenols by this method practical. Long reaction times and relatively high catalysts levels are needed. A catalyst removal step may also be required depending upon the intended end use.

Recent improvements in DMC catalyst technology have provided catalysts with exceptional activity for epoxide polymerization. For example, U.S. Pat. No. 5,470,813 describes substantially amorphous or non-crystalline catalysts that have much higher activities compared with earlier DMC catalysts. Other highly active DMC catalysts include, in addition to a low molecular weight organic complexing agent, from about 5 to about 80 wt. % of a polyether such as a polyoxypropylene polyol (see U.S. Pat. Nos. 5,482,908 and 5,545,601). Even more recently, DMC catalysts that incorporate a functionalized polymer other than a polyether have been described (copending appl. Ser. No. 08/731,495). Highly active DMC catalysts are generally substantially non-crystalline, as is evidenced by powder X-ray diffraction patterns that lack many sharp lines.

Still needed in the art are practical ways to alkoxylate carbonyl-functionalized phenols. A preferred process would give high yields of the alkoxylated phenols and reduced amounts of by-products. Preferably, the process would give low-color products that have low viscosities and low polydispersities. A valuable process would enable efficient preparation of high-quality alkoxylated carbonyl-functionalized phenols having more than about five oxyalkylene units.

SUMMARY OF THE INVENTION

The invention is a process for making an alkoxylated carbonyl-functionalized phenol. The process comprises reacting a carbonyl-functionalized phenol with an alkylene oxide in the presence of a substantially non-crystalline double metal cyanide (DMC) catalyst.

The process of the invention offers surprising and valuable advantages. First, in contrast to the process that uses a conventional DMC catalyst, reaction rates are high, even at relatively low catalyst levels. Thus, reaction times are short, and a catalyst removal step can often be eliminated. Second, the reaction product has low color. This contrasts with the typical base-catalyzed process used to make alkoxylated phenols, which gives a high-color product. Third, the process gives high yields of alkoxylated carbonyl-functionalized phenols and avoids condensation reaction and cyclic ether by-products that plague acid- and base-catalyzed alkoxylations. Fourth, because side reactions are minimal, the process gives a low-viscosity product that has a low polydispersity. Finally, the process enables efficient preparation of alkoxylated carbonyl-functonalized phenols that are valuable in the surfactant industry, such as alkoxylated 4-hydroxy-acetophenones that have five or more oxyalkylene units.

DETAILED DESCRIPTION OF THE INVENTION

In the process of the invention, a carbonyl-functionalized phenol reacts with an alkylene oxide in the presence of a substantially non-crystalline double metal cyanide (DMC) catalyst to produce an alkoxylated carbonyl-functionalized phenol.

By "carbonyl-functionalized phenol," we mean compounds that have at least one phenolic —OH group, and one or more carbonyl functional groups (e.g., aldehyde, ketone, ester) attached to a carbon that has an enolizable hydrogen atom. These carbonyl-functionalized phenols can undergo condensation reactions (e.g., aldol or Dieckmann-type condensations) that compete with phenol alkoxylation when an acid or base catalyst is used. The condensation reactions produce large proportions of side products that contribute high color and high viscosity to the alkoxylated phenol.

Suitable carbonyl-functionalized phenols include, for example, hydroxyacetophenones, hydroxyphenylacetaldehydes, and alkyl esters of hydroxyphenylacetic acid. All of these have at least one enolizable hydrogen atom on a carbon that is alpha to an aldehyde, ketone, or ester carbonyl group. Particularly preferred are hydroxyacetophenones such as 4-hydroxy-acetophenone.

Alkylene oxides suitable for use in the invention include epoxides that can undergo ring-opening polymerization with a DMC catalyst. Examples include ethylene oxide, propylene oxide, butylene oxides, styrene oxide, and the like, and mixtures thereof. When more than one alkylene oxide is used, it can be introduced as a mixture of compounds to give a random copolymer, or in stages to make block copolymers. Control over which alkylene oxides are used, how they are introduced, and ratio of alkylene oxides to phenol are adjusted to achieve, for example, the desired degree of hydrophilicity or hydrophobicity in the alkoxylated carbonyl-functionalized phenol.

A substantially non-crystalline double metal cyanide catalyst is used in the process. By "substantially non-crystalline," we mean lacking a well-defined crystal structure, or characterized by the substantial absence of sharp lines in the powder X-ray diffraction pattern of the composition. Conventional zinc hexacyanocobaltate-glyme catalysts (such as those described in U.S. Pat. No. 5,158, 922) show a powder X-ray diffraction pattern containing many sharp lines, which indicates that the catalyst has a high degree of crystallinity. Zinc hexacyanocobaltate prepared in the absence of a complexing agent is also highly crystalline. In contrast, catalysts used in the process of the invention are substantially non-crystalline.

Several kinds of highly active, substantially non-crystalline DMC catalysts have been described, and these are suitable for use in the process of the invention. For example, U.S. Pat. No. 5,470,813, the teachings of which are incorporated herein by reference, shows how to make substantially non-crystalline DMC compounds using t-butyl alcohol as the preferred complexing agent. Example 2 below shows how to make an alkoxylated phenol with this type of catalyst. U.S. Pat. Nos. 5,482,908 and 5,545,601, the teachings of which are incorporated herein by reference, describe highly active, substantially non-crystalline DMC catalysts that include, in addition to a low molecular weight organic complexing agent, from about 5 to about 80 wt. % of a polyether such as a polyoxypropylene polyol. Example 1 below shows this type of substantially non-crystalline DMC catalyst in a process of the invention. Zinc hexacyanocobaltate catalysts are preferred.

Other suitable non-crystalline DMC catalysts include those that incorporate a functionalized polymer other than a polyether as described in copending appl. Ser. No. 08/731, 495. These catalysts include from about 2 to about 80 wt. % of the functionalized polymer or a water-soluble salt derived from it.

By "functionalized polymer" we mean a polymer, other than a polyether, that contains one or more functional groups containing oxygen, nitrogen, sulfur, phosphorus, or halogen, wherein the polymer, or a water-soluble salt derived from it, has relatively good water solubility, i.e., at least about 3 wt. % of the polymer or its salt dissolves at room temperature in water or mixtures of water with a water-miscible organic solvent. Examples of water-miscible organic solvents are tetrahydrofuran, acetone, acetonitrile, t-butyl alcohol, and the like. Water solubility is important for incorporating the functionalized polymer into the catalyst structure during formation and precipitation of the double metal cyanide compound.

Preferred functionalized polymers have the general structure:

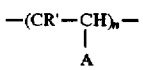

in which R' is hydrogen, —COOH, or a $C_1$–$C_5$ alkyl group, and A is one or more functional groups selected from the group consisting of —OH, —NH$_2$, —NHR, —NR$_2$, —SH, —SR, —COR, —CN, —Cl, —Br, —C$_6$H$_4$—OH, —C$_6$H$_4$—C(CH$_3$)$_2$OH, —CONH$_2$, —CONHR, —CO—NR$_2$, —OR, —NO$_2$, —NHCOR, —NRCOR, —COOH, —COOR, —CHO, —OCOR, —COO—R—OH, —SO$_3$H, —CONH—R—SO$_3$H, pyridinyl, and pyrrolidonyl, in which R is a $C_1$–$C_5$ alkyl or alkylene group, and n has a value within the range of about 5 to about 5,000. More preferably, n is within the range of about 10 to about 500.

Optionally, the functionalized polymer also includes recurring units derived from a non-functionalized vinyl monomer such as an olefin or diene, e.g., ethylene, propylene, butylenes, butadiene, isoprene, styrene, or the like, provided that the polymer or a salt derived from it has relatively good solubility in water or mixtures of water and a water-miscible organic solvent.

Suitable functionalized polymers include, for example, poly(acrylamide), poly(acrylamide-co-acrylic acid), poly (acrylic acid), poly(2-acrylamido-2-methyl-1-propanesulfonic acid), poly(acrylic acid-co-maleic acid), poly(acrylonitrile), poly(alkyl acrylate)s, poly(alkyl methacrylate)s, poly(vinyl methyl ether), poly(vinyl ethyl ether), poly(vinyl acetate), poly(vinyl alcohol), poly(N-vinylpyrrolidone), poly(N-vinylpyrrolidone-co-acrylic acid), poly(N,N-dimethylacrylamide), poly(vinyl methyl ketone), poly(4-vinylphenol), poly(4-vinylpyridine), poly (vinyl chloride), poly(acrylic acid-co-styrene), poly(vinyl sulfate), poly(vinyl sulfate) sodium salt, and the like.

The functionalized polymer can also be a polymer selected from the group consisting of polyesters, polycarbonates, oxazoline polymers, polyalkylenimines, maleic acid and maleic anhydride copolymers, hydroxyethyl cellulose, starches, and polyacetals. Thus, the functionalized polymer can be, for example, poly(ethylene glycol adipate), poly(dipropylene glycol adipate), poly(1,6-hexanediol carbonate), poly(2-ethyl-2-oxazoline), poly(vinyl butyral-co-vinyl alcohol-co-vinyl acetate), and the like, and salts thereof.

The molecular weight of the functionalized polymer can vary over a fairly wide range. Preferably, the number average molecular weight is within the range of about 300 to about 500,000; a more preferred range is from about 500 to about 50,000.

DMC catalysts used in the process of the invention include an organic complexing agent. Generally, the complexing agent is relatively soluble in water. Suitable complexing agents are those commonly known in the art, as taught, for example, in U.S. Pat. No. 5,158,922. The complexing agent is added either during preparation or immediately following precipitation of the catalyst. Usually, an excess amount of the complexing agent is used. Preferred complexing agents are water-soluble heteroatom-containing organic compounds that can complex with the double metal cyanide compound. Suitable complexing agents include, but are not limited to, alcohols, aldehydes, ketones, ethers, esters, amides, ureas, nitriles, sulfides, and mixtures thereof. Preferred complexing agents are water-soluble aliphatic alcohols selected from the group consisting of ethanol, isopropyl alcohol, n-butyl alcohol, isobutyl alcohol, sec-butyl alcohol, and tert-butyl alcohol. Tert-butyl alcohol is most preferred.

The reaction products made by the process of the invention are alkoxylated carbonyl-functionalized phenols. These result from addition of oxyalkylene units to the phenolic hydroxyl group of the carbonyl-functionalized phenol. The reaction products retain most or all of the carbonyl functionality of the starting phenol.

Preferred alkoxylated carbonyl-functionalized phenols made by the process of the invention have the structure:

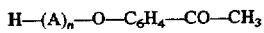
H—(A)$_n$—O—C$_6$H$_4$—CO—CH$_3$ in which A is an oxyalkylene group, and n has a value within the range of about 5 to about 50. More preferably, n has a value within the range of about 10 to about 30. Preferably, A is an oxypropylene group.

The process of the invention offers surprising and valuable advantages. First, reaction rates are high, even at relatively low catalyst levels. As Examples 1–4 and Comparative Example 5 below show, substantially non-crystalline DMC catalysts are highly active compared with a conventional zinc hexacyanocobaltate-glyme complex. In fact, with the older catalyst, the reaction time required is unacceptably long. In addition, the low catalyst levels used with non-crystalline DMC catalysts often eliminate any need to remove it from the alkoxylated phenol. With earlier catalysts, a back-end purification step was usually needed.

A second advantage of the process is reaction products with low color. This contrasts with the typical base-catalyzed process used to make alkoxylated phenols, which gives a high-color product. Compare the products from Examples 1–4 (slightly yellow) with that of Comparative Example 6 (red). The process of the invention therefore obviates a need to decolorize the alkoxylated phenol, for example, by carbon treatment or vacuum distillation.

Third, the process gives high yields of alkoxylated carbonyl-functionalized phenols and avoids condensation reaction and cyclic ether by-products that plague acid- and base-catalyzed alkoxylations. While phenols are usually alkoxylated with base catalysts, the use of a DMC catalyst offers the clear advantage of better selectivity to alkoxylated phenols.

Fourth, because side reactions are minimal, the process gives a low-viscosity product that has a low polydispersity. Low viscosity is a processing advantage, while low polydispersity often contributes to better physical properties.

Finally, the process enables efficient preparation of alkoxylated carbonyl-functonalized phenols that are valuable in the surfactant industry, such as alkoxylated 4-hydroxy acetophenones that have five or more oxyalkylene units. These products are hard to make by conventional processes, particularly when propylene oxide is used to alkoxylate the phenol, because the side reactions become more dominant. As the examples below illustrate, side reactions devalue the base-catalyzed synthesis of propoxylated 4-hydroxyacetophenone (Comparative Example 6), while the process of the invention (Examples 1–4) gives a much cleaner product (compare NMR, HPLC, and infrared results).

The following examples merely illustrate the invention; those skilled in the art will recognize many variations that are within the spirit of the invention and scope of the claims.

EXAMPLE 1

Preparation of Propoxylated 4-Hydroxyacetophenone using a Polyether-Containing, Non-crystalline Zinc Hexacyanocobaltate Catalyst A one-liter stirred reactor is charged with 4-hydroxacetophenone (100 g), and zinc hexacyanocobaltate/ t-butyl alcohol complex that incorporates about 25 wt. % of a 1000 mol. wt. polyoxypropylene diol (0.030 g, prepared as described in U.S. Pat. No. 5,482,908). The stirred mixture is heated to 130° C. The reactor is evacuated, and propylene oxide (18 g) is added. The initial reactor pressure is 10 psig, but drops to 0 psig after 15 min. Additional propylene oxide (10 g) is added, and pressure drops as before. The process is repeated until 88 g of propylene oxide have been added and the catalyst has become fully activated. The remaining 338 g of propylene oxide (426 g total) is then fed continuously at 6 g/min. After the addition is complete, the reactor is held at 130° C. until a constant pressure is observed. Residual unreacted monomer is removed by stripping under vacuum at 80° C. The resulting product (496 g) is slightly yellow. Viscosity (25° C.): 288 cps. Hydroxyl number: 83.0 mg KOH/g. Gel permeation chromatography shows: Mn=776; Mw/Mn= 1.04. NMR and infrared spectra are consistent with a propoxylated 4-hydroxyacetophenone having an average of about 10 oxypropylene units per molecule.

EXAMPLE 2

Preparation of Propoxylated 4-Hydroxyacetophenone using a Substantially Non-crystalline Zinc Hexacyanocobaltate Catalyst The procedure of Example 1 is followed, except that the catalyst used is a substantially non-crystalline zinc hexacyanocobaltate/ t-butyl alcohol complex prepared as described in Example A below.

A total of 429 g of propylene oxide is used. The resulting product (506 g) is slightly yellow. Viscosity (25° C.): 280 cps. Hydroxyl number: 80.0 mg KOH/g. Gel permeation chromatography shows: Mn=722; Mw/Mn=1.03. NMR and infrared spectra are consistent with a propoxylated 4-hydroxyacetophenone having an average of about 10 oxypropylene units per molecule.

EXAMPLE A

Catalyst Preparation: Substantially Non-Crystalline Zinc Hexacyanocobaltate/ t-Butyl Alcohol Complex A round-bottom flask equipped with mechanical stirrer, addition funnel, and thermometer is charged with distilled water (302 mL), potassium hexacyanocobaltate (7.4 g), and t-butyl alcohol (39 g). The mixture is stirred until all of the potassium salt dissolves. The resulting solution is heated to 30° C. To the stirred solution is added 152 g of a 50/50 (wt/wt) solution of zinc chloride in water over 50 min. Stirring continues for another 30 min. at 30° C. The resulting white suspension is filtered under pressure at 30 psig. An 8.0-g portion of the filter cake is resuspended with vigorous stirring in a solution of t-butyl alcohol (110 g) and water (60 mL). After all of the solids are completely suspended in the wash solution, stirring continues for 30 min. The mixture is

EXAMPLE 3
Preparation of Propoxylated 4-Hydroxyacetophenone using a Substantially Non-crystalline Zinc Hexacyanocobaltate Catalyst The procedure of Example 1 is followed, except that the catalyst used is a substantially non-crystalline zinc hexacyanocobaltate/ t-butyl alcohol complex containing tetraethylene glycol dimethacrylate prepared as described in Example B below.

The catalyst becomes completely active after adding 72 g of propylene oxide. A total of 428 g of propylene oxide is used. The resulting product (500 g) is slightly yellow. Viscosity (25° C.): 275 cps. Hydroxyl number: 81.4 mg KOH/g. Gel permeation chromatography shows: Mn=709; Mw/Mn=1.03. NMR and infrared spectra are consistent with a propoxylated 4-hydroxyacetophenone having an average of about 10 oxypropylene units per molecule.

EXAMPLE B
Catalyst Preparation: Zinc Hexacyanocobaltate/ t-Butyl Alcohol Complex Containing a Functionalized Polymer Zinc chloride solution (120 g of 62.5 wt. % $ZnCl_2$ in water) is dissolved in distilled water (230 mL) and t-butyl alcohol (50 mL) to give Solution 1. Solution 2 is made by dissolving potassium hexacyanocobaltate (7.5 g) in distilled water (100 mL). Solution 3 is made by mixing tetra(ethylene glycol) dimethacrylate (8.0 g) in a 12:1 (vol/vol) mixture of distilled water and tetrahydrofuran (52 mL). Solution 2 is added to Solution 1 over 30 min. at 50° C. while homogenizing the mixture at 20% of maximum mixing intensity. Mixing intensity is increased to 40% for the next 10 min. of mixing. The homogenizer is stopped. Solution 3 is added to the mixture, which is stirred magnetically for 3 min., and is then pressure filtered through a 20 micron filter at 40 psig. The filter cake is reslurried in t-butyl alcohol (130 mL) and distilled water (55 mL), and the mixture is homogenized for 10 min. at 40% intensity. The homogenizer is stopped. Additional tetra(ethylene glycol) dimethacrylate (2.0 g) is added, and the mixture is stirred magnetically for 3 min. The mixture is pressure filtered as described above. The filter cake is reslurried in t-butyl alcohol (185 mL), and is homogenized at 40% intensity for 10 min. The homogenizer is stopped. Additional tetra(ethylene glycol) dimethacrylate (1.0 g) is added, and the mixture is stirred magnetically for 3 min. Filtration and isolation of the catalyst proceeds as previously described. The cake is dried under vacuum at 60° C. to constant weight.

EXAMPLE 4
Preparation of Propoxylated 4-Hydroxyacetophenone using a Polyether-Containing, Non-crystalline Zinc Hexacyanocobaltate Catalyst The procedure of Example 1 is generally followed, except that toluene (100 g) is included in the initial charge to the reactor. The mixture is initially heated to 110° C. with stirring. The reactor is evacuated and propylene oxide (50 g) is added. The initial pressure is 26 psig. After 45 min., the reactor pressure drops to 10 psig, and more propylene oxide (25 g) is added. After another 20 min., the reactor pressure drops to -2.5 psig. The rest of the propylene oxide is then continuously added as in Example 1. A total of 426 g of propylene oxide is used.

Unreacted monomer and toluene are removed in the usual way by stripping. The resulting product (504 g) is slightly yellow. Viscosity (25° C.): 270 cps. Hydroxyl number: 79.9 mg KOH/g. Gel permeation chromatography shows: Mn=726; Mw/Mn=1.03. NMR and infrared spectra are consistent with a propoxylated 4-hydroxyacetophenone having an average of about 10 oxypropylene units per molecule.

COMPARATIVE EXAMPLE 5
Preparation of Propoxylated 4-Hydroxyacetophenone using a Conventional Zinc Hexacyanocobaltate / Glyme Catalyst The procedure of Example 1 is generally followed except that the catalyst used is a conventional zinc hexacyanocobaltate / glyme catalyst prepared as described in U.S. Pat. No. 5,158,922.

The reactor is charged with 4-hydroxyacetophenone (150 g) and the catalyst (0.39 g). The reactor is evacuated and propylene oxide (39 g) is added. The initial reactor pressure is 20 psig. After 60 min., the reactor pressure drops to 4 psig. and additional propylene oxide (15 g) is added. After another 70 min., the reactor pressure drops again. The process is repeated until 170 g of propylene oxide has been added. The catalyst requires 7 hours to become activated. The remaining propylene oxide is added continuously at 6 g/min. A total of 630 g of propylene oxide is used.

The resulting product (741 g) is slightly yellow. Viscosity (25° C.): 275 cps. Hydroxyl number: 94.1 mg KOH/g. Gel permeation chromatography shows: Mn=647; Mw/Mn=1.11. NMR and infrared spectra are consistent with a propoxylated 4-hydroxyacetophenone having an average of about 10 oxypropylene units per molecule.

This example demonstrates that conventional DMC catalysts can be used to make propoxylated 4-hydroxyacetophenone, but high catalyst levels are needed, and the reaction initiates too sluggishly to be commerically practical. In addition, a catalyst removal step might be required.

COMPARATIVE EXAMPLE 6
Base-Catalyzed Preparation of Propoxylated 4-Hydroxyacetophenone A two-step process is used. In step one, a potassium phenolate salt of 4-hydroxyacetophenone is made. Next, the phenolate salt reacts with propylene oxide to give propoxylated 4-hydroxyacetophenone.

A one-liter three-neck flask equipped with a reflux condenser and magnetic stirrer is charged with 4-hydroxyacetophenone (111 g), potassium hydroxide (54.6 g), and isopropyl alcohol (600 mL). The mixture is heated to reflux (85° C.) for 1 h, and all of the solids dissolve. Upon cooling to room temperature, yellow crystals form. The solids are isolated by filtration and are dried under vacuum overnight. Yield of potassium phenolate salt: 98 g.

A one-liter stirred reactor is charged with N,N-dimethylformamide (100 g) and a portion (60 g) of the potassium phenolate salt prepared above. The reactor is evacuated briefly, and the mixture is heated with stirring to 120° C. Propylene oxide (200 g) is fed to the reactor at 2 g/min. The final reactor pressure reaches 24 psig. After propylene oxide addition is complete, the mixture is held at 120° C. for 80 min., and the reactor pressure drops to 0 psig. Residual unreacted monomer and solvent are then stripped under vacuum at 120° C. The resulting product (223 g) is a red liquid. Viscosity (25° C.): 1275 cps. Hydroxyl number: 139 mg KOH/g. Gel permeation chromatography shows: Mn=365; Mw/Mn=1.84. NMR and HPLC analysis show that the product contains many impurities. The proposed structure is inconsistent with the NMR and infrared results. The infrared spectrum shows that little carbonyl content remains in the product.

The preceding examples are meant only as illustrations; the following claims define the scope of the invention.

We claim:

1. A process comprising reacting a carbonyl-functionalized phenol with an alkylene oxide in the presence of a substantially non-crystalline double metal cyanide (DMC) catalyst to produce an alkoxylated carbonyl-functionalized phenol.

2. The process of claim 1 wherein the carbonyl-functionalized phenol is 4-hydroxyacetophenone.

3. The process of claim 1 wherein the alkoxylated carbonyl-functionalized phenol has the structure:

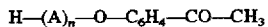

in which A is an oxyalkylene group, and n has a value within the range of about 5 to about 50.

4. The process of claim 3 wherein the carbonyl-functionalized phenol is 4-hydroxyacetophenone, A is an oxypropylene group, and n has a value within the range of about 10 to about 30.

5. The process of claim 1 wherein the alkylene oxide is selected from the group consisting of ethylene oxide, propylene oxide, butylene oxides, and mixtures thereof.

6. The process of claim 1 wherein the catalyst is a zinc hexacyanocobaltate.

7. The process of claim 1 wherein the catalyst is a zinc hexacyanocobaltate /t-butyl alcohol complex.

8. The process of claim 1 wherein the catalyst incorporates a polymer selected from the group consisting of polyethers and functionalized polymers.

9. A process comprising reacting a carbonyl-functionalized phenol with propylene oxide in the presence of a substantially non-crystalline double metal cyanide (DMC) catalyst to produce a propoxylated carbonyl-functionalized phenol.

10. The process of claim 9 wherein the carbonyl-functionalized phenol is 4-hydroxyacetophenone.

11. The process of claim 9 wherein the propoxylated carbonyl-functionalized phenol has the structure:

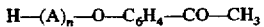

in which A is an oxypropylene group, and n has a value within the range of about 5 to about 50.

12. The process of claim 11 wherein the carbonyl-functionalized phenol is 4-hydroxyacetophenone, and n has a value within the range of about 10 to about 30.

13. The process of claim 9 wherein the catalyst is a zinc hexacyanocobaltate.

14. The process of claim 9 wherein the catalyst is a zinc hexacyanocobaltate /t-butyl alcohol complex.

15. The process of claim 9 wherein the catalyst incorporates a polymer selected from the group consisting of polyethers and functionalized polymers.

16. A process comprising reacting 4-hydroxyacetophenone with propylene oxide in the presence of a substantially non-crystalline zinc hexacyanocobaltate catalyst to produce a propoxylated 4-hydroxyacetophenone of the structure:

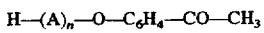

in which A is an oxypropylene group, and n has a value within the range of about 10 to about 30.

17. The process of claim 16 wherein the catalyst is a zinc hexacyanocobaltate /t-butyl alcohol complex.

18. The process of claim 16 wherein the catalyst incorporates a polymer selected from the group consisting of polyethers and functionalized polymers.

19. An alkoxylated carbonyl-functionalized phenol made by the process of claim 1.

* * * * *